United States Patent

Thiele et al.

[11] Patent Number: 4,505,737
[45] Date of Patent: Mar. 19, 1985

[54] SYNERGISTIC HERBICIDAL COMPOSITIONS

[75] Inventors: Gerald H. Thiele, Sunnyvale, Calif.; David L. Stamp, Albion, Nebr.

[73] Assignee: Stauffer Chemical Company, Westport, Conn.

[21] Appl. No.: 236,969

[22] Filed: Feb. 23, 1981

Related U.S. Application Data

[63] Continuation of Ser. No. 108,602, Jan. 17, 1980, abandoned, which is a continuation-in-part of Ser. No. 15,553, Feb. 26, 1979, abandoned.

[51] Int. Cl.³ .................... A01N 57/00; A01N 43/36
[52] U.S. Cl. .................................... 71/86; 71/95
[58] Field of Search ....................... 71/95, 86

[56] References Cited

U.S. PATENT DOCUMENTS

| | | | |
|---|---|---|---|
| 3,879,188 | 4/1975 | Fritz et al. | 71/86 |
| 4,110,105 | 8/1978 | Teach | 71/95 |
| 4,132,713 | 1/1979 | Broadhurst | 71/95 |
| 4,152,429 | 5/1979 | Hayakawa et al. | 71/86 |
| 4,160,659 | 7/1979 | Rodebush et al. | 71/95 |
| 4,203,253 | 5/1980 | Wolter et al. | 71/86 |
| 4,238,219 | 12/1980 | Holm et al. | 71/86 |
| 4,328,026 | 5/1982 | Kliegman et al. | 71/86 |

FOREIGN PATENT DOCUMENTS 2006740  5/1979  United Kingdom .................. 71/86

OTHER PUBLICATIONS

Amann, Aqueous Sprayable Mixtures, etc., (1971), CA 77, No. 1855j, (1972).
Carson et al., "Influence of Ethephon, etc.," (1975), CA 83, No. 127394a, (1975).

*Primary Examiner*—Glennon H. Hollrah
*Attorney, Agent, or Firm*—Paul R. Martin; M. Henry Heines

[57] ABSTRACT

Synergistic herbicidal activity is displayed by compositions comprising the following two components:
(a) a pyrrolidone of the formula

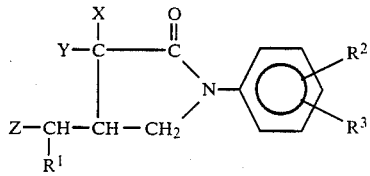

in which X is selected from the group consisting of hydrogen, chlorine and methyl; Y is selected from the group consisting of hydrogen, chlorine and bromine; Z is selected from the group consisting of chlorine and bromine; $R^1$ is selected from the group consisting of hydrogen and $C_1$-$C_4$ alkyl; $R^2$ is selected from the group consisting of hydrogen, halogen, $C_1$-$C_4$ alkyl, acetyl, trifluoromethyl, nitro, cyano, $C_1$-$C_4$ alkoxy, $C_1$-$C_4$ alkylthio, $C_1$-$C_4$ alkylsulfinyl, $C_1$-$C_4$ alkylsulfonyl, trifluoromethylsulfinyl, trifluoromethylsulfonyl, pentafluoropropionamido, and 3-methylureido; and $R^3$ is selected from the group consisting of hydrogen, $C_1$-$C_4$ alkyl, chlorine and trifluoromethyl; and
(b) a phosphonic acid of the formula

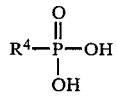

in which $R^4$ is selected from the group consisting of $C_1$-$C_4$ alkyl, $C_1$-$C_4$ haloalkyl, and —$CH_2NHCH_2COOH$, at a weight ratio of (a) to (b) of from about 0.1:1 to about 20:1.

4 Claims, No Drawings

SYNERGISTIC HERBICIDAL COMPOSITIONS

CROSS REFERENCE TO RELATED APPLICATIONS

This application is a continuation of application Ser. No. 108,602, filed Jan. 17, 1980, now abandoned, which is a continuation-in-part of application Ser. No. 015,553, filed Feb. 26, 1979 both now abandoned.

BACKGROUND OF THE INVENTION

The protection of crops from weeds and other vegetation which inhibit crop growth by consuming valuable acreage or soil nutrients is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In many cases, active herbicides have been shown to be more effective in combination than when applied individually. The result is often termed "synergism", since the combination demonstrates a potency or activity level exceeding that which it would be expected to have, based on a knowledge of the individual potencies of the components. The present invention resides in the discovery that certain pyrrolidones and certain phosphonic acids, already known individually for their herbicidal potency, display this synergistic effect when applied in combination.

PRIOR ART

The two classes of compounds forming the combination which is the subject of the present invention are independently known in the art as active herbicides. Pyrrolidones are disclosed as herbicides in U.S. Pat. No. 4,110,105 (Teach, Aug. 29, 1979), and phosphonic acids are similarly disclosed in U.S. Pat. Nos. 3,853,530 (Franz, Dec. 10, 1974), 3,799,758 (Franz, Mar. 26, 1974), and 3,929,450 (Hamm, Dec. 30, 1975), as well as numerous other references including Maynard et al., "Organophosphorus Compounds. I. 2-Chloroalkylphosphonic Acids as Phosphorylating Agents," Aust. J. Chem., 16, 596–608 (1963), and Yang, "Ethylene Evolution From 2-Chloroethylphosphonic Acid," Plant Physiol., 44, 1203–1204 (1969).

DESCRIPTION OF THE INVENTION

It has now been found that synergism in the control of undesirable vegetation is exhibited by compositions comprising a mixture of the following two components:
(a) a pyrrolidone of the formula

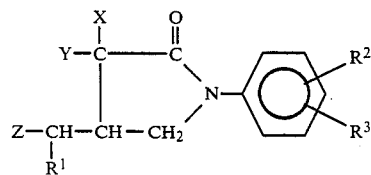

in which
X is selected from the group consisting of hydrogen, chlorine and methyl;
Y is selected from the group consisting of hydrogen, chlorine and bromine;
Z is selected from the group consisting of chlorine and $C_1$–$C_4$ alkyl;
$R_1$ is selected from the group consisting of hydrogen and $C_1$–$C_4$ alkyl;
$R^2$ is selected from the group consisting of hydrogen, halogen, $C_1$–$C_4$ alkyl, acetyl, trifluoromethyl, nitro, cyano, $C_1$–$C_4$ alkoxy, $C_1$–$C_4$ alkylthio, $C_1$–$C_4$ alkylsulfinyl, $C_1$–$C_4$ alkylsulfonyl, trifluoromethylthio, trifluoromethylsulfinyl, trifluoromethylsulfonyl, pentafluoropropionamido, and 3-methylureido; and
$R^3$ is selected from the group consisting of hydrogen, $C_1$–$C_4$ alkyl, chlorine and trifluoromethyl; and
(b) a phosphonic acid of the formula

in which $R^4$ is selected from the group consisting of $C_1$–$C_4$ alkyl, $C_1$–$C_4$ haloalkyl, and —$CH_2NHCH_2COOH$.

In the compositions of the present invention, pyrrolidones of the following formula are preferred:

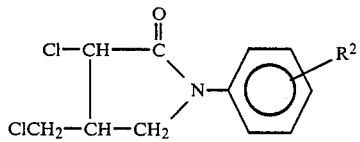

in which $R^2$ is trifluoromethyl or cyano.

The term "alkyl" as used herein includes both straight-chain and branched-chain groups. The carbon atom ranges are intended to be inclusive of both upper and lower limits.

The terms "synergism" and "synergistic" are used herein to convey the result observed when a combination of herbicides demonstrates a potency in excess of that which the combination would be expected to produce on the basis of the potencies of each herbicide applied individually.

The term "herbicide" is used herein to denote a compound which controls or modifies the growth of plants. The term "herbicidally effective amount" is used to indicate the quantity of such a compound or combination of such compounds which is capable of producing a controlling or modifying effect. Controlling or modifying effects include all deviations from natural development, for example, killing, retardation, defoliation, desiccation, regulation, stunting, tillering, stimulating, leaf burn, dwarfing and the like. The term "plants" is used to include germinating seeds, emerging seedlings and established vegetation, including roots and aboveground portions.

In the compositions of this invention, the (pyrrolidone):(phosphonic acid) weight ratio at which the herbicidal response is synergistic lies within the range of about 0.1:1 to about 20:1, preferably about 0.1:1 to about 10:1.

Application rates will depend upon the weeds to be controlled and the degree of control desired. In general, the compositions of this invention are most efficiently employed at a rate of 0.01 to 50 pounds per acre (0.011 to 56 kilograms per hectare) of the active ingredient, preferably 0.1 to 25 pounds per acre (0.11 to 28 kilograms per hectare).

Examples of pyrrolidones useful in the present invention are:
1-phenyl-3-chloro-4-chloromethyl-2-pyrrolidone
1-phenyl-3,3-dichloro-4-chloromethyl-2-pyrrolidone
1-(2',6'-dimethylphenyl)-3-chloro-4-chloromethyl-2-pyrrolidone
1-m-chlorophenyl-3-chloro-4-chloromethyl-2-pyrrolidone
1-p-chlorophenyl-3-chloro-4-chloromethyl-2-pyrrolidone
1-m-trifluoromethylphenyl-3-chloro-4-chloromethyl-2-pyrrolidone
1-phenyl-3-chloro-3-methyl-4-chloromethyl-2-pyrrolidone
1-(3',4'-dichlorophenyl)-3,3-dichloro-4-chloromethyl-2-pyrrolidone
1-m-trifluoromethylphenyl-3,3-dichloro-4-chloromethyl-2-pyrrolidone
1-m-trifluoromethylphenyl-3-chloro-3-methyl-4-chloromethyl-2-pyrrolidone
1-p-tolyl-3-chloro-4-chloromethyl-2-pyrrolidone
1-m-fluorophenyl-3-chloro-4-chloromethyl-2-pyrrolidone
1-m-trifluoromethyl-3-bromo-4-bromomethyl-2-pyrrolidone
1-(3',4'-dichlorophenyl)-3-chloro-4-chloromethyl-2-pyrrolidone
1-m-nitrophenyl-3-chloro-4-chloromethyl-2-pyrrolidone
1-(3',5'-dichlorophenyl)-3-chloro-4-chloromethyl-2-pyrrolidone
1-m-trifluoromethylphenyl-3-chloro-4-(1'-chloroethyl)-2-pyrrolidone
1-m-cyanophenyl-3-chloro-4-chloromethyl-2-pyrrolidone
1-(3',5'-dichlorophenyl)-3,3-dichloro-4-chloromethyl-2-pyrrolidone
1-m-trifluoromethylphenyl-3,3-dichloro-4-(1'-chloroethyl)-2-pyrrolidone
1-m-cyanophenyl-3,3-dichloro-4-chloromethyl-2-pyrrolidone
1-(3'-trifluoromethyl-4'-chlorophenyl)-3-chloro-4-chloromethyl-2-pyrrolidone
1-(3'-trifluoromethyl-4'-chlorophenyl)-3,3-dichloro-4-chloromethyl-2-pyrrolidone
1-m-trifluoromethylthiophenyl-3-chloro-4-chloromethyl-2-pyrrolidone
1-m-methylthiophenyl-3-chloro-4-chloromethyl-2-pyrrolidone
1-m-trifluoromethylsulfinylphenyl-3-chloro-4-chloromethyl-2-pyrrolidone
1-m-methylsulfinylphenyl-3-chloro-4-chloromethyl-2-pyrrolidone
1-m-methylsulfonylphenyl-3-chloro-4-chloromethyl-2-pyrrolidone
1-m-trifluoromethylsulfonylphenyl-3-chloro-4-chloromethyl-2-pyrrolidone
1-(3',5'-bis-trifluoromethylphenyl)-3-chloro-4-chloromethyl-2-pyrrolidone
1-m-methoxyphenyl-3-chloro-4-chloromethyl-2-pyrrolidone
1-m-acetylphenyl-3-chloro-4-chloromethyl-2-pyrrolidone
1-m-tolyl-3-chloro-4-chloromethyl-2-pyrrolidone
1-m-trifluoromethylphenyl-4-chloromethyl-2-pyrrolidone
1-m-bromophenyl-3-chloro-4-chloromethyl-2-pyrrolidone
1-o-chlorophenyl-3-chloro-4-chloromethyl-2-pyrrolidone
1-m-iodophenyl-3-chloro-4-chloromethyl-2-pyrrolidone
1-methoxyphenyl-3-chloro-4-chloromethyl-2-pyrrolidone
1-o-trifluoromethylphenyl-3-chloro-4-chloromethyl-2-pyrrolidone
1-m-pentafluoropropionamidophenyl-3-chloro-4-chloromethyl-2-pyrrolidone
cis-1-m-trifluoromethylphenyl-3-chloro-4-chloromethyl-2-pyrrolidone
trans-1-m-trifluoromethylphenyl-3-chloro-4-chloromethyl-2-pyrrolidone These and other pyrrolidones within the scope of the invention can be prepared by the procedures described in U.S. Pat. No. 4,110,105.

Examples of substituted phosphonic acids useful in the present invention are:
methylphosphonic acid
ethylphosphonic acid
propylphosphonic acid
butylphosphonic acid
t-butylphosphonic acid
s-butylphosphonic acid
2-chloroethylphosphonic acid
2-bromoethylphosphonic acid
N-phosphonomethylglycine These and other substituted phosphonic acids within the scope of the invention can be prepared by the procedures described in U.S. Pat. No. 3,799,758 and the Maynard et al. article mentioned above.

The following examples provide further illustration demonstrating the synergistic herbicidal response of the present inventions.

EXAMPLE I

This example demonstrates the synergistic response of 1-m-trifluoromethylphenyl-3-chloro-4-chloromethyl-2-pyrrolidone and 2-chloroethylphosphonic acid in combined postemergence application to a variety of weeds.

Aluminum flats measuring 15.2×22.9×7.0 centimeters (cm) were filled to a depth of 5.0 cm with loamy sand soil containing 50 parts per million (ppm) each of the commercial fungicide cis-N[(trichloromethyl)thio]-4-cyclohexene-1,2-dicarboximide (Captan®) and 18—18—18 fertilizer (percentages of N—$P_2O_5$—$K_2O$ on a weight basis). Several rows were impressed across the width of each flat and each row was seeded with a single weed species. The weed species included yellow nutsedge (Cyperus esculentus), nightshade (Solanum nigrum) johnsongrass (Sorghum halepense), wild oat (Avena fatua), velvetleaf (Abutilon theophrasti), jimsonweed (Datura stramonium), and annual morning glory (Ipomoea purpurea). Ample seeds were planted to give about 20 to 50 seedlings per row after emergence depending on the size of the plants. The flats were then placed in a greenhouse for two weeks, where they were watered regularly.

At the end of this period, the foliage on the emergent weeds was sprayed with aqueous solutions of the test compounds. The quantities sprayed were such that the amount of each test compound applied per flat corresponded to the desired application rate in pounds per acre. In control flats, the test compounds were applied alone at various application rates, whereas in the test flats, solutions containing both compounds were applied. Additional flats not treated at all were used as a standard for measuring the extent of weed control occurring in the treated flats.

Three weeks after treatment, the control and test flats were compared to the standard and each row was rated visually in terms of percent control ranging from 0% to 100%, with 0% representing the same degree of growth as the same row in the standard and 100% representing complete kill of all weeds in the row. All types of plant injury were taken into consideration.

The results of these tests are listed in Table I in the columns headed by the symbol "O" (indicating the "observed" results). These results are compared with the expected results, shown in the columns headed by the symbol "E", derived from the control data using Limpel's formula (Limpel et al., 1962, "Weed Control by Dimethylchloroterephahalate Alone and in Certain Combinations," Proc. NEWCC, Vol. 16, pp 48-53):

$$E = X + Y - (XY/100)$$

where

X = observed percent injury when one of the herbicides is used alone, and

Y = observed percent injury when the other herbicide is used alone.

An asterisk (*) is used to indicate the tests where the results show synergism, i.e., where the observed result exceeds the expected result. Since synergism can only be detected when the expected result is less than 100, tests where both the E and O values are 100 are left blank.

It is clear from the table that synergism was widely evident over the entire range of application rates tested.

TABLE I

HERBICIDE SYNERGISM TEST RESULTS

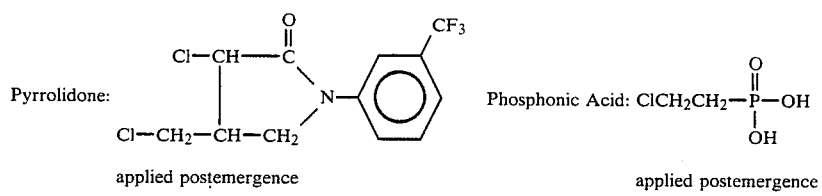

Pyrrolidone (applied postemergence); Phosphonic Acid: $ClCH_2CH_2-P(=O)(OH)_2$ (applied postemergence)

| Application Rates (lb/A) | | Percent Control - O: Observed  E: Expected | | | | | | | | | | | | | |
|---|---|---|---|---|---|---|---|---|---|---|---|---|---|---|
| | | Nightshade | | Jimsonweed | | Velvetleaf | | Nutsedge | | Morningglory | | Johnsongrass | | Wild Oat | |
| Pyrrolidone | Phosphonic Acid | O | E | O | E | O | E | O | E | O | E | O | E | O | E |
| Control Data: | | | | | | | | | | | | | | | |
| 0.25 | — | 20 | | 30 | | 20 | | 0 | | 0 | | 5 | | 0 | |
| 0.5 | — | 40 | | 65 | | 60 | | 10 | | 10 | | 15 | | 20 | |
| 1.0 | — | 95 | | 100 | | 98 | | 40 | | 30 | | 60 | | 40 | |
| — | 0.25 | 0 | | 0 | | 0 | | 0 | | 0 | | 0 | | 0 | |
| — | 0.5 | 0 | | 0 | | 0 | | 0 | | 0 | | 0 | | 0 | |
| — | 1.0 | 10 | | 30 | | 0 | | 0 | | 0 | | 10 | | 0 | |
| Test Data: | | | | | | | | | | | | | | | |
| 0.25 | 0.25 | 40* | 20 | 100* | 30 | 20* | 20 | 0 | 0 | 0 | 0 | 0 | 5 | 0 | 0 |
| 0.25 | 0.5 | 60* | 20 | 100* | 30 | 40* | 20 | 0 | 0 | 10* | 0 | 0 | 5 | 0 | 0 |
| 0.25 | 1.0 | 70* | 28 | 100* | 51 | 100* | 20 | 0 | 0 | 20* | 0 | 20* | 15 | 30* | 0 |
| 0.5 | 0.25 | 80* | 40 | 100* | 65 | 85* | 60 | 0 | 10 | 20* | 10 | 30* | 15 | 20 | 20 |
| 0.5 | 0.5 | 100* | 40 | 100* | 65 | 100* | 60 | 10 | 10 | 20* | 10 | 65* | 15 | 25* | 20 |
| 0.5 | 1.0 | 100* | 46 | 100* | 76 | 100* | 60 | 10 | 10 | 30* | 10 | 60* | 24 | 30* | 20 |
| 1.0 | 0.25 | 100* | 95 | | | | | 40 | 40 | 20 | 30 | 90* | 60 | 50* | 40 |
| 1.0 | 0.5 | 100* | 95 | | | | | 60* | 40 | 25 | 30 | 98* | 60 | 100* | 40 |
| 1.0 | 1.0 | 100* | 96 | | | | | 65* | 40 | 30 | 30 | 98* | 64 | 100* | 40 |

*Synergistic effect shown. Blank spaces indicate 100% control in both observed and expected results, precluding evaluation of synergism.

EXAMPLE II

In this example, the same herbicides used in Example I were used. Here, however, the pyrrolidone was applied in pre-emergence fashion: it was sprayed over the soil surface on the same day on which the weed seeds were planted, i.e., before the weeds were able to emerge from the soil. The phosphonic acid was applied in post-emergence fashion as in Example I. The application rates were varied somewhat to show a wider range and the injury ratings were taken four weeks after planting rather than five. Otherwise, the procedures were identical to those of Example I.

The results are shown in Table II, where a strong degree of synergism is evident at higher application rates.

TABLE II

HERBICIDE SYNERGISM TEST RESULTS

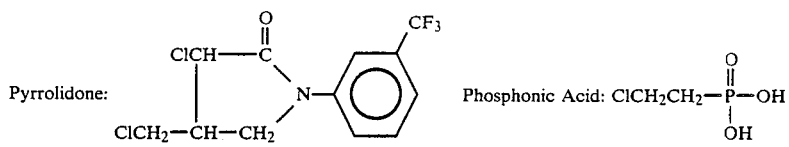

Pyrrolidone: (structure shown)     Phosphonic Acid: $ClCH_2CH_2-\overset{\overset{O}{\|}}{\underset{OH}{P}}-OH$ applied pre-emergence          applied postemergence

| Application Rates (lb/A) | | Percent Control - O: Observed E: Expected | | | | | | | | | | | | | |
|---|---|---|---|---|---|---|---|---|---|---|---|---|---|---|---|
| | | Night-shade | | Jimson-weed | | Velvet-leaf | | Nutsedge | | Morning-glory | | Johnson-grass | | Wild Oat | |
| Pyrrolidone | Phosphonic Acid | O | E | O | E | O | E | O | E | O | E | O | E | OO | E |
| Control Data: | | | | | | | | | | | | | | | |
| 0.0625 | — | 0 | | 0 | | 10 | | 0 | | 0 | | 10 | | 0 | |
| 0.125 | — | 30 | | 20 | | 30 | | 0 | | 10 | | 20 | | 10 | |
| 0.25 | — | 50 | | 60 | | 65 | | 10 | | 40 | | 30 | | 20 | |
| — | 0.5 | 0 | | 0 | | 0 | | 0 | | 0 | | 0 | | 0 | |
| — | 1.0 | 0 | | 0 | | 0 | | 0 | | 0 | | 0 | | 0 | |
| — | 2.0 | 0 | | 0 | | 0 | | 0 | | 0 | | 0 | | 0 | |
| Test Data: | | | | | | | | | | | | | | | |
| 0.0625 | 0.5 | 0 | 0 | 0 | 0 | 10 | 10 | 0 | 0 | 0 | 0 | 0 | 10 | 0 | 0 |
| 0.0625 | 1.0 | 0 | 0 | 0 | 0 | 10 | 10 | 0 | 0 | 0 | 0 | 0 | 10 | 0 | 0 |
| 0.0625 | 2.0 | 0 | 0 | 0 | 0 | 10 | 10 | 0 | 0 | 0 | 0 | 0 | 10 | 0 | 0 |
| 0.125 | 0.5 | 30 | 30 | 20 | 20 | 30 | 30 | 0 | 0 | 10 | 10 | 10 | 20 | 10 | 10 |
| 0.125 | 1.0 | 30 | 30 | 20 | 20 | 30 | 30 | 0 | 0 | 10 | 10 | 10 | 20 | 10 | 10 |
| 0.125 | 2.0 | 30 | 30 | 20 | 20 | 30 | 30 | 0 | 0 | 10 | 10 | 10 | 20 | 10 | 10 |
| 0.25 | 0.5 | 100* | 50 | 60 | 60 | 100* | 65 | 10 | 10 | 40 | 40 | 100* | 30 | 30* | 20 |
| 0.25 | 1.0 | 100* | 50 | 65* | 60 | 100* | 65 | 10 | 10 | 40 | 40 | 100* | 30 | 60* | 20 |
| 0.25 | 2.0 | 100* | 50 | 70* | 60 | 100* | 65 | 10 | 10 | 40 | 40 | 100* | 30 | 65* | 20 |

*Synergistic effect shown.

EXAMPLE III

This example demonstrates the synergistic response of 1-m-trifluoromethylphenyl-3-chloro-4-chloromethyl-2-pyrrolidone and N-phosphonomethylglycine in combined postemergence application.

The weed species used in this test included shattercane (*Sorghum bicolor*) and annual ryegrass (*Lolium multiflorum*) as well as the yellow nutsedge, wild oat, johnsongrass, and annual morning glory species listed above. Fiber flats were used rather than aluminum. The emergent weeds were treated three weeks after seeding and injury ratings were taken four weeks later. Otherwise, the procedure was the same as that described in Example I.

The results are shown in Table III, where a strong degree of synergism is evident in many of the tests.

TABLE III

HERBICIDE SYNERGISM TEST RESULTS

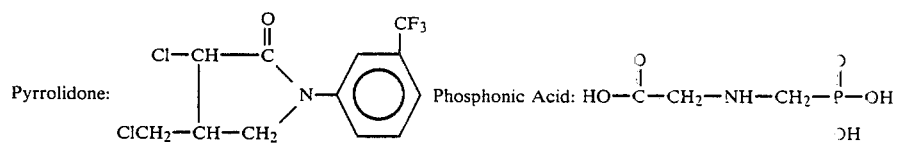

Pyrrolidone: (structure shown)     Phosphonic Acid: $HO-\overset{\overset{O}{\|}}{C}-CH_2-NH-CH_2-\overset{\overset{O}{\|}}{\underset{OH}{P}}-OH$ applied postemergence          applied postemergence

| Application Rates (lb/A) | | Percent Control - O: Observed E: Expected | | | | | | | | | | | |
|---|---|---|---|---|---|---|---|---|---|---|---|---|---|
| | | Shatter-cane | | Nutsedge | | Ryegrass | | Morning-glory | | Wild Oat | | Johnson-grass | |
| Pyrrolidone | Phosphonic Acid | O | E | O | E | O | E | O | E | O | E | O | E |
| Control Data: | | | | | | | | | | | | | |
| 0.125 | — | 10 | | 0 | | 0 | | 0 | | 10 | | 10 | |
| 0.25 | — | 20 | | 0 | | 30 | | 0 | | 60 | | 40 | |
| 0.5 | — | 30 | | 10 | | 65 | | 0 | | 70 | | 70 | |
| — | 0.125 | 0 | | 70 | | 40 | | 0 | | 0 | | 0 | |
| — | 0.25 | 0 | | 70 | | 60 | | 0 | | 20 | | 0 | |
| — | 0.5 | 65 | | 80 | | 90 | | 30 | | 30 | | 0 | |
| Test Data: | | | | | | | | | | | | | |
| 0.125 | 0.125 | 10 | 10 | 30 | 70 | 40 | 40 | 0 | 0 | 40* | 10 | 100* | 0 |
| 0.125 | 0.25 | 0 | 10 | 75* | 70 | 70* | 60 | 20* | 0 | 100* | 37 | 100* | 0 |
| 0.125 | 0.5 | 50 | 69 | 75 | 80 | 95* | 90 | 60* | 30 | 100* | 64 | 100* | 0 |
| 0.25 | 0.125 | 20 | 20 | 50 | 70 | 70* | 58 | 60* | 0 | 100* | 60 | 100* | 40 |
| 0.25 | 0.25 | 20 | 20 | 60 | 70 | 95* | 72 | 60* | 0 | 100* | 72 | 90* | 40 |
| 0.25 | 0.5 | 60 | 72 | 70 | 80 | 98* | 93 | 100* | 30 | 100* | 84 | 70* | 40 |
| 0.5 | 0.125 | 40* | 30 | 80* | 76 | 70 | 79 | 40* | 0 | 100* | 70 | 100* | 70 |

TABLE III-continued
HERBICIDE SYNERGISM TEST RESULTS

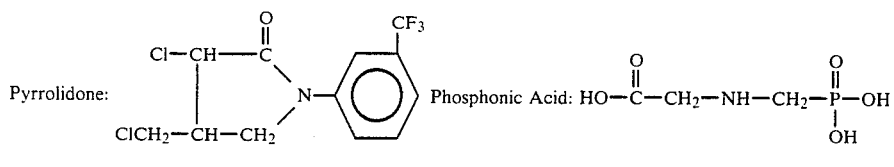

Pyrrolidone: applied postemergence
Phosphonic Acid: applied postemergence

| Application Rates (lb/A) | | Percent Control - O: Observed E: Expected | | | | | | | | | | |
|---|---|---|---|---|---|---|---|---|---|---|---|---|
| | | Shatter-cane | | Nutsedge | | Ryegrass | | Morning-glory | | Wild Oat | | Johnson-grass |
| Pyrrolidone | Phosphonic Acid | O | E | O | E | O | E | O | E | O | E | O | E |
| 0.5 | 0.25 | 30 | 30 | 60 | 76 | 70 | 86 | 50* | 0 | 100* | 79 | 60 | 60 |
| 0.5 | 0.5 | 40 | 76 | 98* | 84 | 99* | 97 | 75* | 30 | 100* | 88 | 100* | 60 |

*Synergistic effect shown.

EXAMPLE IV

The same herbicides tested in Example III were tested in the data shown in this example, the main difference being that the pyrrolidone was applied pre-emergence, rather than postemergence with the phosphonic acid. The latter was applied two weeks after planting, and injury ratings were taken two weeks later. The procedure was otherwise identical to that of Example I.

The results are shown in Table IV, where synergism is indicated at all application rates.

and N-phosphonomethylglycine in combined postemergence application. The weed species included watergrass (*Echinochloa crusgalli*), foxtail (*Setaria viridis*) in addition to the wild oat, yellow nutsedge, annual morning glory, and annual ryegrass previously tested, in fiber flats. The weeds were treated ten days after seeding, and injury ratings were taken 17 days later. Since the tests were performed during the winter season, low growth rates occurred rendering comparisons with the standard more difficult. Synergism, however, is shown in many of the tests results, which are listed in Table V.

TABLE VI
HERBICIDE SYNERGISM TEST RESULTS

Pyrrolidone: applied preemergence
Phosphonic Acid: applied postemergence

| Application Rates (lb/A) | | Percent Control - O: Observed E: Expected | | | | | | | | | | | |
|---|---|---|---|---|---|---|---|---|---|---|---|---|---|
| | | Night-shade | | Jimson-weed | | Velvet-leaf | | Nutsedge | | Morning-glory | | Johnson-grass | | Wild Oat | |
| Pyrrolidone | Phosphonic Acid | O | E | O | E | O | E | O | E | O | E | O | E | O | E |
| Control Data: | | | | | | | | | | | | | | | | |
| 0.0625 | — | 0 | | 0 | | 10 | | 0 | | 0 | | 10 | | 0 | |
| 0.125 | — | 30 | | 20 | | 30 | | 0 | | 10 | | 20 | | 10 | |
| 0.25 | — | 50 | | 60 | | 65 | | 10 | | 40 | | 30 | | 20 | |
| — | 0.125 | 30 | | 20 | | 0 | | 10 | | 10 | | 0 | | 0 | |
| — | 0.25 | 60 | | 30 | | 20 | | 20 | | 15 | | 10 | | 0 | |
| — | 0.5 | 100 | | 50 | | 100 | | 40 | | 30 | | 60 | | 100 | |
| Test Data: | | | | | | | | | | | | | | | | |
| 0.0625 | 0.125 | 75* | 30 | 20 | 20 | 0 | 10 | 10 | 10 | 10 | 10 | 10 | 10 | 10 | 0 |
| 0.0625 | 0.25 | 100* | 60 | 30 | 30 | 40* | 28 | 30* | 20 | 10 | 15 | 15 | 19 | 40 | 0 |
| 0.0625 | 0.5 | | | 60* | 50 | | | 50* | 40 | 40* | 30 | 60 | 64 | 65 | 100 |
| 0.125 | 0.125 | 100* | 51 | 20 | 36 | 20 | 30 | 10 | 10 | 10 | 19 | 40* | 20 | 20* | 10 |
| 0.125 | 0.25 | 100* | 72 | 30 | 44 | 60* | 44 | 40* | 20 | 20 | 24 | 60* | 28 | 40* | 10 |
| 0.125 | 0.5 | | | 100* | 60 | | | 90* | 40 | 30 | 37 | 85* | 68 | | |
| 0.25 | 0.125 | 100* | 65 | 40 | 68 | 100* | 65 | 30* | 19 | 40 | 46 | 100* | 30 | 100* | 20 |
| 0.25 | 0.25 | 100* | 85 | 50 | 72 | 100* | 72 | 60* | 28 | 50* | 49 | 100* | 37 | 95* | 20 |
| 0.25 | 0.5 | | | 60 | 80 | | | 75* | 46 | 60* | 58 | 100* | 72 | | |

*Synergistic effect shown.
Blank spaces indicate 100% control in both observed and expected results, precluding synergism evaluation.

EXAMPLE V

The tests shown in this example were run with 1-m-cyanophenyl-3-chloro-4-chloromethyl-2-pyrrolidone

TABLE V
HERBICIDE SYNERGISM TEST RESULTS

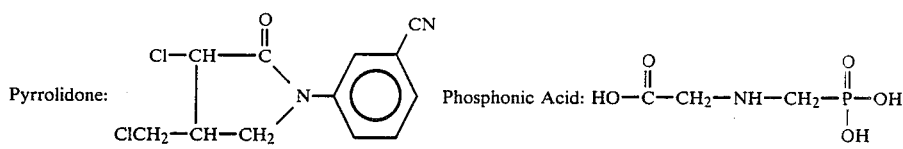

Pyrrolidone: applied postemergence

Phosphonic Acid: applied postemergence

| Application Rates (lb/A) | | Percent Control - O: Observed E: Expected | | | | | | | | | | | |
|---|---|---|---|---|---|---|---|---|---|---|---|---|---|
| | | Wild Oat | | Water-grass | | Nut-sedge | | Morning-glory | | Rye-grass | | Foxtail | |
| Pyrrolidone | Phosphonic Acid | O | E | O | E | O | E | O | E | O | E | O | E |
| Control Data: | | | | | | | | | | | | | |
| 0.062 | — | 0 | | 0 | | 0 | | 0 | | 0 | | 0 | |
| 0.125 | — | 0 | | 0 | | 0 | | 0 | | 0 | | 0 | |
| 0.25 | — | 0 | | 0 | | 0 | | 0 | | 0 | | 30 | |
| — | 0.125 | 0 | | 0 | | 0 | | 0 | | 0 | | 50 | |
| — | 0.25 | 0 | | 0 | | 0 | | 0 | | 0 | | 65 | |
| — | 0.5 | 0 | | 0 | | 20 | | 10 | | 0 | | 75 | |
| Test Data: | | | | | | | | | | | | | |
| 0.062 | 0.125 | 0 | 0 | 0 | 0 | 0 | 0 | 10* | 0 | 0 | 0 | 40 | 50 |
| 0.062 | 0.25 | 0 | 0 | 0 | 0 | 40* | 0 | 20* | 0 | 20* | 0 | 65* | 60 |
| 0.062 | 0.5 | 0 | 0 | 20* | 0 | 60* | 20 | 30* | 10 | 40* | 0 | 75 | 75 |
| 0.125 | 0.125 | 0 | 0 | 0 | 0 | 0 | 0 | 0 | 0 | 0 | 0 | 50 | 50 |
| 0.125 | 0.25 | 0 | 0 | 0 | 0 | 0 | 0 | 0 | 0 | 0 | 0 | 50 | 60 |
| 0.125 | 0.5 | 0 | 0 | 0 | 0 | 20 | 20 | 10 | 10 | 10* | 0 | 60 | 75 |
| 0.25 | 0.125 | 0 | 0 | 0 | 0 | 0 | 0 | 0 | 0 | 0 | 0 | 30 | 65 |
| 0.25 | 0.25 | 0 | 0 | 0 | 0 | 10* | 0 | 20* | 0 | 10* | 0 | 60 | 76 |
| 0.25 | 0.5 | 0 | 0 | 40* | 0 | 60* | 20 | 30* | 10 | 30* | 0 | 100* | 83 |

*Synergistic effect shown.

The compositions of this invention are useful as herbicides demonstrating synergistic activity for the control of undesirable vegetation. The compositions can be formulated in the same manner in which herbicides are generally formulated. The compounds may be applied either separately or combined as part of a two-part herbicidal system.

The object of the formulation is to apply the compositions to the locus where control is desired by a convenient method. The "locus" may include soil, seeds, seedlings, and vegetation.

Formulations will generally contain several additives. Among these are some inert ingredients and diluent carriers such as organic solvents, water, oil and water, water in oil emulsions, carriers of dust and granules, and surface active, wetting, dispersing, and emulsifying agents.

Fertilizers, e.g., ammonium nitrate, urea and superphosphate may also be added.

Aids to rooting and growth, e.g., compost, manure, humus, sand, etc., may likewise be added.

The formulations are commonly dusts, wettable powders, granules, solutions of emulsifiable concentrates.

Dusts are free-flowing powder compositions containing the herbicidal compound impregnated on a particulate carrier. The particle size of the carrier is usually in the approximate range of 30 to 50 microns. Examples of suitable carriers are talc, bentonite, diatomaceous earth, and pyrophyllite. Anticaking and antistatic agents can be added, if desired. The composition generally contains up to 50% of active ingredient. Dusts, like liquid compositions, can be applied from boom and hand or power sprayers or airplanes.

Wettable powders are finely divided compositions comprising a particulate carrier impregnated with the herbicide compound and additionally containing one or more surface active agents. The surface active agent promotes rapid dispersion of the powder in aqueous medium to form stable, sprayable suspensions. A wide variety of surface active agents can be used, for example, long chain fatty alcohols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, Pesticide Formulations, (Marcel Dekker, Inc., N.Y., 1973) at pages 79-84.

Granules comprise the herbicidal composition impregnated on a particulate inert carrier having a particle size of about 1 to 2 millimeters in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

It is not necessary that the compositions be admixed with the soil particles. After application by the above discussed methods, they may be distributed below the surface to a depth of at least one-half inch by conventional means such as discing, dragging, or mixing.

The compositions of this invention can also be applied by addition to irrigation water supplied to the field to be treated. This method of application permits the penetration of the compositions into the soil as the water is absorbed therein.

What is claimed is:

1. A synergistic herbicidal composition consisting essentially of a mixture of
   (a) an effective amount of a pyrrolidone of the formula

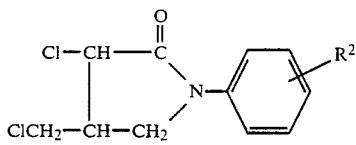

in which $R^2$ is trifluoromethyl, and
   (b) an effective amount of a phosphonic acid of the formula

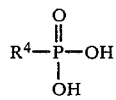

in wich $R^4$ is $C_1$–$C_4$ haloalkyl, at a weight ratio of (a) to (b) of from about 1:8 to about 4:1.

2. A composition according to claim 1 in which $R^2$ is m-trifluoromethyl and $R^4$ is 2-chloroethyl.

3. A method of controlling undesirable vegetation which comprises applying to the locus where control is desired a herbicidally effective amount of a composition consisting essentially of a mixture of
   (a) an effective amount of a pyrrolidone of the formula

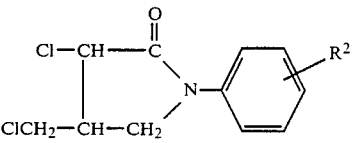

in which $R^2$ is trifluoromethyl, and
   (b) an effective amount of a phosphonic acid of the formula

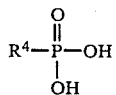

in wich $R^4$ is $C_1$–$C_4$ haloalkyl, at a weight ratio of (a) to (b) of from about 1:8 to about 4:1.

4. A method according to claim 3 in which $R^2$ is m-trifluoromethyl and $R^4$ is 2-chloroethyl.

* * * * *